(12) United States Patent
Verjus et al.

(10) Patent No.: US 7,175,601 B2
(45) Date of Patent: Feb. 13, 2007

(54) PORTABLE EQUIPMENT FOR MEASURING AND/OR MONITORING THE HEART RATE

(75) Inventors: Christophe Verjus, Neuchatel (CH); Rolf Vetter, Yverdon (CH); Patrick Celka, Forel (CH); Philippe Renevey, Lausanne (CH)

(73) Assignee: CSEM Centre Suisse d'Electronique et de Microtechnique S.A.-Recherche et Developpement, Neuchatel (CH)

( * ) Notice: Subject to any disclaimer, the term of this patent is extended or adjusted under 35 U.S.C. 154(b) by 547 days.

(21) Appl. No.: 10/463,530

(22) Filed: Jun. 18, 2003

(65) Prior Publication Data

US 2003/0233051 A1    Dec. 18, 2003

(30) Foreign Application Priority Data

Jun. 18, 2002    (FR) .................................. 02 07465

(51) Int. Cl.
*A61B 5/02* (2006.01)
(52) U.S. Cl. ....................... 600/500; 600/485
(58) Field of Classification Search .................... None
See application file for complete search history.

(56) References Cited

U.S. PATENT DOCUMENTS

| | | | | |
|---|---|---|---|---|
| 4,301,808 A | * | 11/1981 | Taus | 600/500 |
| 5,413,101 A | * | 5/1995 | Sugiura | 600/323 |
| 5,431,170 A | * | 7/1995 | Mathews | 600/479 |
| 6,080,110 A | * | 6/2000 | Thorgersen | 600/500 |
| 6,230,047 B1 | * | 5/2001 | McHugh | 600/519 |
| 6,283,915 B1 | * | 9/2001 | Aceti et al. | 600/300 |

FOREIGN PATENT DOCUMENTS

| | | |
|---|---|---|
| EP | 0 923 903 | 6/1999 |
| EP | 0 941 694 | 9/1999 |
| EP | 1 297 784 | 4/2003 |
| WO | 97/14357 | 4/1997 |
| WO | 99/32030 | 7/1999 |

\* cited by examiner

*Primary Examiner*—Robert L. Nasser
(74) *Attorney, Agent, or Firm*—Jacobson Holman PLLC

(57) ABSTRACT

Portable equipment including in combination a heart rate measuring device and a sound reproduction unit including means for supplying a signal representative of the sound reproduction and for supplying sound information to a sound transducer, wherein said measuring device and said sound transducer are mounted at least in part in an assembly adapted to be fixed to an ear of a wearer of the equipment and, wherein said sound reproduction unit includes means for optionally substituting for and/or superimposing on said signal representative of said sound reproduction a signal generated from signals from said measuring device and representative of said heart rate. The equipment can take the form of a walkman, for example, or a hearing aid for the hard of hearing.

10 Claims, 2 Drawing Sheets

PORTABLE EQUIPMENT FOR MEASURING AND/OR MONITORING THE HEART RATE

FIELD OF THE INVENTION

The present invention relates to portable equipment for optically measuring and/or monitoring the heart rate.

BACKGROUND OF THE INVENTION

Many variants of this type of equipment exist already. They include an optical probe designed to be placed on a region of the skin of a user. The probe includes an emitter for radiating light into the tissue of that region and a receiver for picking up energy coming from the tissue (for example as a result of reflection on the tissue or transmission through the tissue) whose optical characteristics vary in dependence upon the circulation of the blood. The signal supplied by the receiver is analyzed and artifacts caused in particular by the movements of the user, ambient light, etc. are removed in an electronic processing unit whose output signal can be made perceptible in any appropriate manner, for example by displaying it on a screen, by reproducing it audibly, etc. The output signal can be compared to a threshold and an alarm tripped if the heart rate crosses the threshold.

Equipment having the above features is described in EP 01203686.9, filed Sep. 28, 2001 and entitled "Wrist located pulse detection using infra-red signals, activity and nonlinear artefact cancellation". That document describes in particular a probe intended to be worn on the wrist, the useful signal being extracted by a device for detecting movements of the wearer.

In another prior art device, the probe is incorporated into a chest strap and the useful signal is transmitted by radio to a display device, such as a wristwatch.

An object of the invention is to provide equipment of the kind indicated above that provides reliable information concerning the heart rate of the wearer whilst being convenient to use and particularly suitable for use by persons exercising an activity, for example a sports activity.

SUMMARY OF THE INVENTION

The invention therefore provides a portable equipment including in combination a measuring device for measuring the heart rate and a sound reproduction unit including means for supplying a signal representative of the sound reproduction and for supplying sound information to a sound transducer, wherein said measuring device and said sound transducer are mounted at least in part in an assembly adapted to be fixed to an ear of a wearer of the equipment, wherein said sound reproduction unit includes substitution/superimposition means for optionally substituting for and/or superimposing on said signal representative of said sound reproduction a signal generated from signals from said measuring device and representative of said heart rate, wherein said assembly takes the form of an ear cushion including a casing accommodating said sound transducer and adapted to be placed in front of the external auditory meatus opening of a wearer and a horn attached to said casing and adapted to be placed behind the external ear of a wearer and said measuring device is accommodated at least in part in said casing and at least in part in said horn, and wherein said assembly further includes an accelerometric device delivering motion signals representative of the motion of a wearer when the assembly is fixed to an ear of said wearer and said measuring device including signal processing means using said motion signals for removing at least partially artifacts due to motion in said signal representative of said heart rate.

Because of the above features, the heart rate measuring function can be associated with that of a sound reproduction device, like for example a walkman. Sound reproduction devices of this kind are very widely used, especially by persons exercising a sporting activity. The information concerning the heart rate can therefore be provided as a complement to the reproduced sound signal, which is generally entertaining and that the wearer of the equipment is used to listening to. Also, the complementary information is presented by means of a sound reproduction component (an ear cushion) that is of the usual kind and is placed over the ear of the wearer of the equipment in the usual way, the exterior shape of the probe placed over the ear being intentionally no different from that of a standard ear cushion. Furthermore, the heart rate measurement function is implemented very discreetly, which users of the equipment may see as an advantage. It will finally be noted that an ear cushion is held in place without problems despite the movements of the wearer, while the connection between the ear cushion and the body of the walkman is not modified either (at least externally), and requires only a connecting cable slightly modified compared to the usual cable. It can therefore be very robust.

In addition prior art portable devices which are in the form of an ear clip, besides the fact they pinch the ear lobe and therefore hinder its vascularization, are fixed on a flexible part of the ear (the ear lobe) and it is therefore difficult to remove in such devices the artifacts due to the motion of the body of the wearer. According to the present invention, the detecting unit being incorporated in an ear cushion, it is advantageously adapted to be worn in contact with a stiff part of the ear (the cartilage) and therefore it becomes easier to remove the artefacts due to the motion of the body.

According to other advantageous features of the invention:

said measuring device includes an optical radiation emitter and an optical radiation receiver respectively placed in said casing and in said horn so that a light path between them can pass through a portion of the external ear of a wearer, said optical radiation emitter includes a plurality of light sources emitting at separate wavelengths that are preferably near infra-red wavelengths, said receiver includes the same number of groups of optical radiation detectors as there are light sources in said emitter and said measuring device further includes means for calculating the average of signals supplied by the detectors of each group, said substitution/superimposition means of said sound reproduction unit include a mixer circuit adapted to receive said signal representative of said heart rate supplied by said measuring device and connected between said sound transducer and said means supplying said signal representative of the sound reproduction, said sound reproduction unit includes voice synthesizer means connected between said probe and said mixer circuit, said portable equipment further includes a comparator having a first input adapted to receive said signal representative of said heart rate and a second input connected to a threshold generator whose threshold is representative of a predetermined heart rate value and whose output is connected to said mixer circuit to send alarm information to said sound transducer if the heart rate supplied by said measuring device exceeds said predetermined heart rate value, a selector is adapted to select reproduction by said sound transducer either of said alarm information or of said signal representative of said heart rate supplied by said measuring device, said sound reproduction unit includes a reader of a sound information medium, such as an audio cassette, a compact disc or a digital versatile disc, connected to said assembly by a cable, said sound reproduction unit includes a microphone and constitutes a hearing aid.

Other features and advantages of the present invention will become apparent in the course of the following description, which is given by way of example only and with reference to the appended drawings.

DETAILED DESCRIPTION OF THE PREFERRED EMBODIMENTS

Figure 1:
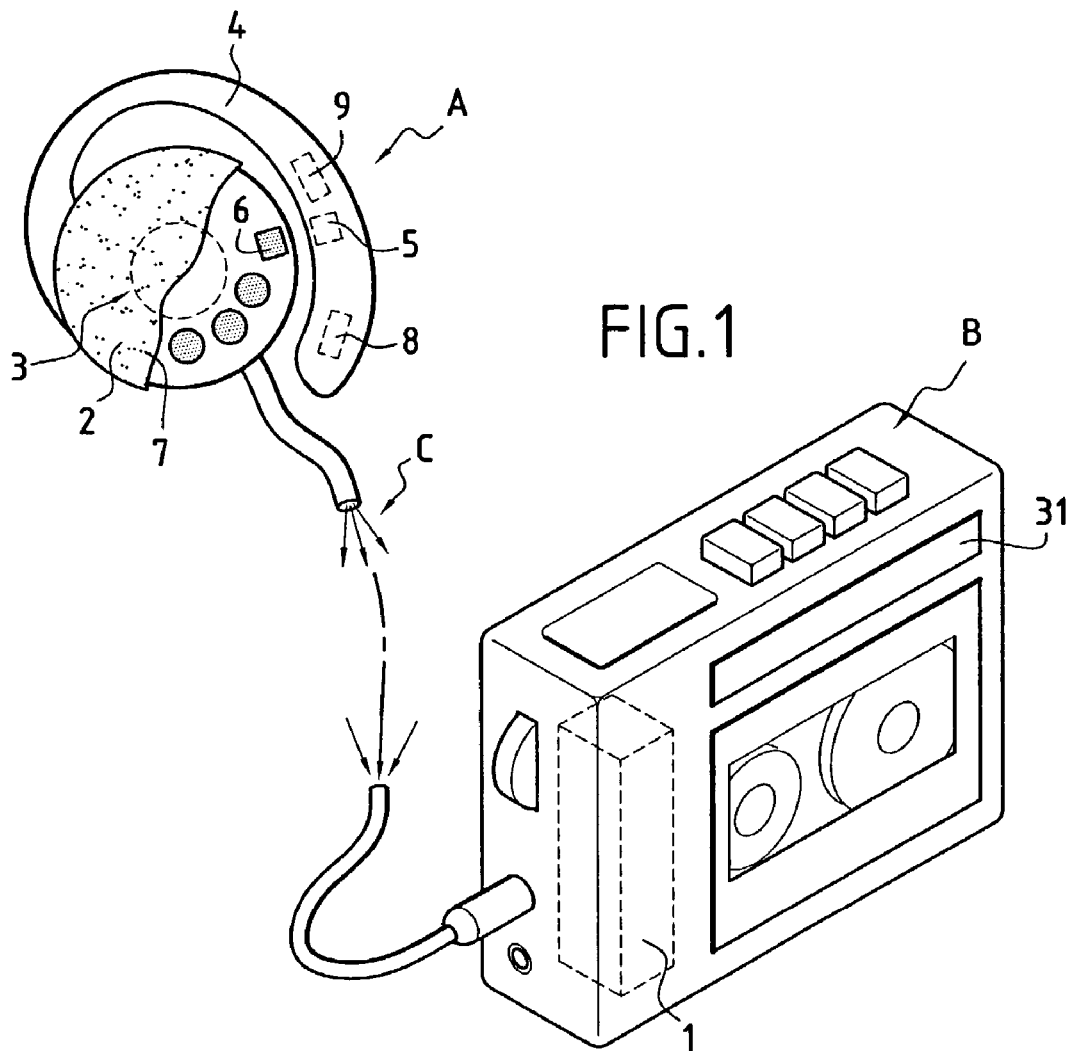
FIG. 1 is a diagrammatic representation of portable sound reproduction equipment combined with a heart rate measuring and/or monitoring function.

FIG. 1 shows a first embodiment of portable equipment according to the invention.

The equipment comprises a first unit A adapted in particular to measure the heart rate and a second sound reproduction unit B adapted in particular to reproduce sound, the two units being interconnected by a cable C. In the embodiment shown, the unit B is an audiocassette player, preferably adapted to be easily worn by a user, as is usual for the devices usually known as "walkmans". Of course, the invention applies to other sound reproduction devices using other recording media, such as compact disks (CD), digital versatile disks (DVD), etc. The cassette player B is of standard design and is therefore not described in detail. Suffice to say that its sound reproduction electrical circuit has added components that are schematically represented in FIG. 1 by a functional unit 1 that is described later.

The unit A takes the form of an ear cushion comprising a generally circular casing 2 adapted to be placed inside the external ear (auricle) of a user in front of the external auditory meatus opening, the side of the casing 2 that can be seen in FIG. 1 facing toward the latter opening. The casing 2 of the ear cushion contains a sound transducer symbolized by the dashed line circle 3. This transducer is conventional, and any design available off the shelf may be used.

The casing 2 is fastened to a horn 4 whose free end part is adapted to hook behind the external ear of a user, as is usual for ear cushions used with off the shelf walkmans. An optical emitter 5 is placed in the horn 4 so that it directs radiation toward the casing 2. In other words, looking at FIG. 1, the emitter 5 is on the non visible side of the horn 4.

An optical radiation receiver 6 is disposed in the casing 2 so that it can pick up the portion of the optical radiation emitted by the emitter 5 that has passed through the thickness of the external ear. Consequently, the received radiation is a function of variations in the optical characteristics of the portion of the external ear through which the radiation has passed, which variations are caused in particular by variations in the circulation of blood in the external ear. The variations in the electrical signal delivered by the receiver 6 are therefore representative in particular of the pulsation of the blood and therefore of the heart rate.

The casing 2 can be covered with a foam material cushion 7 (only part of which is shown) to protect the portion of the ear surrounding the external auditory meatus opening.

An accelerometric device 8 is placed in the horn 4 for measuring acceleration along three axes. Its function is explained later.

Figure 2:
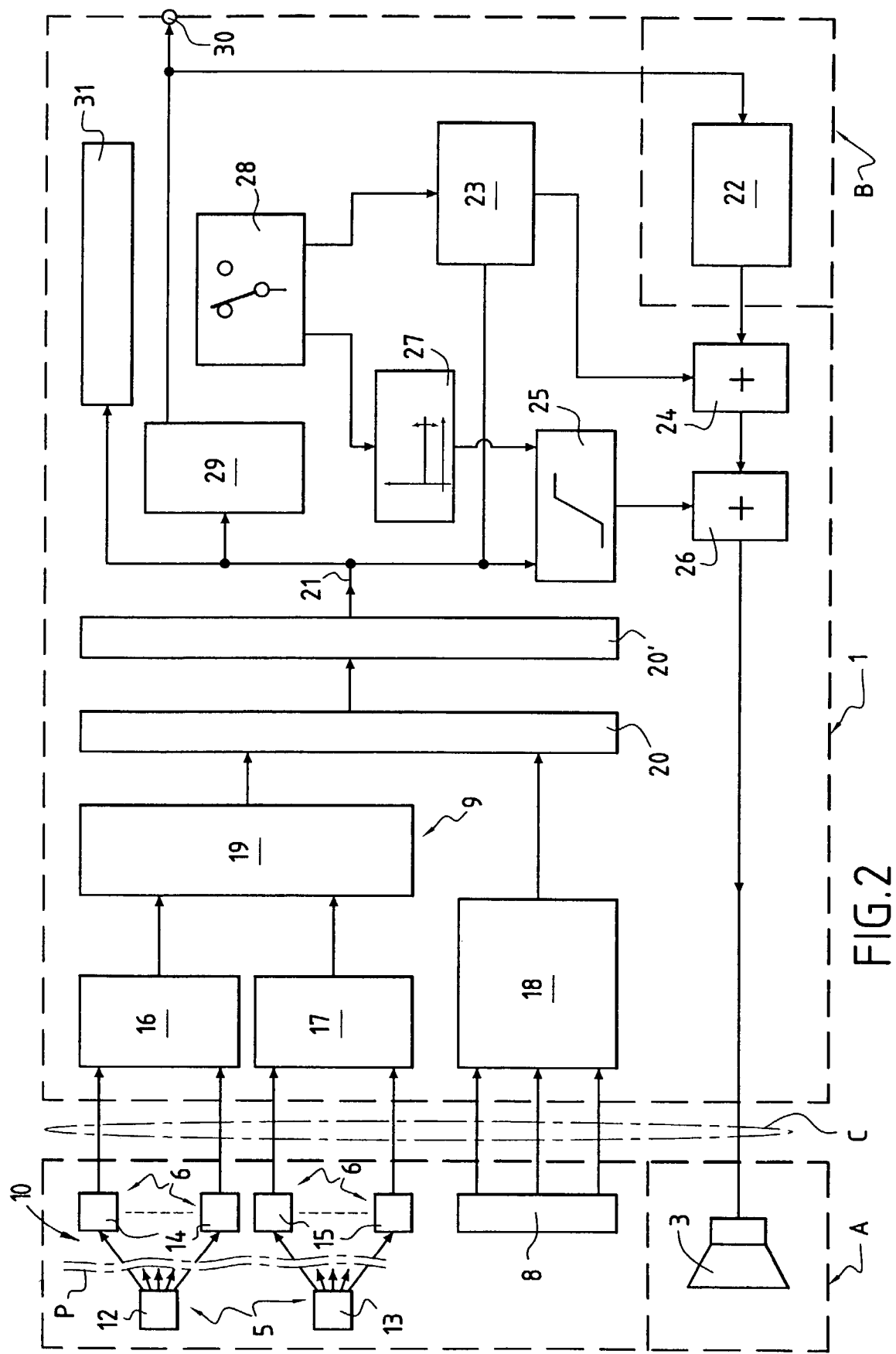
FIG. 2 is a block diagram of the equipment shown in FIG. 1.

FIG. 2 is a block diagram of the equipment shown in FIG. 1. It shows that the unit A comprises the sound reproduction transducer 3 and a measuring probe 10 which comprises the emitter 5, the receiver 6 and the accelerometric device 8. The emitter 5 comprises one or more sources of optical radiation (two sources 12 and 13 in the example shown) emitting at two different wavelengths, for example, in this example two wavelengths $\lambda_1$ and $\lambda_2$. These sources irradiate a portion P of the cartilage of the external ear. As already described, the receiver 6 is on the opposite side of this portion P of the external ear when the ear cushion is in place thereon.

In corresponding relationship to each source 12, 13, the receiver 6 comprises respectively a plurality of optical detectors 14 and 15, whose sensitivity ranges are adjusted to the respective wavelengths of the sources 12 and 13. In one embodiment, the sources 12 and 13 are modulated by a control signal so as to be active alternately. Wideband receivers 14 and 15 can then be used and a time division demultiplexing enables to retrieve the two-optical signals with wavelengths $\lambda_1$ and $\lambda_2$.

In the preferred embodiment of the invention, the wavelengths $\lambda_1$ and $\lambda_2$ are near infra-red wavelengths, the sources are light-emitting diodes, and the detectors are photosensitive diodes.

The outputs of the group of detectors 14 and 15, of the accelerometric device 8 and of the transducer 3 are connected by a cable C to a processing unit, designated with the general reference 9 and integrated into the functional unit 1 incorporated in the unit B. In the context of the present invention, the combination of the processing unit 9 and the measuring probe 10 is referred to as "heart rate measuring device".

The detectors 14 and 15 are respectively connected to signal filtering means 16 and signal shaping means 17 in the processing unit 9. The filtering can be carried out by an analog band-pass filter with a pass-band from 0.5 Hz to 10 Hz, for example. Shaping of the signals can involve averaging the analog signal supplied by each detector 14 and 15 and appropriately amplifying the signals.

The signals generated by the accelerometric device 8 are applied to signal filtering and shaping means 18 that apply filtering and amplification on these signals, the filtering being performed by means of an analog band-pass filter whose passband is from 0.5 Hz to 10 Hz, for example.

The signals processed in this way in the units 16 and 17 are fed to a circuit 19 for eliminating unwanted artifacts in which they are subject to analog/digital conversion and to treatment for eliminating artifacts that may be that described in the document WO 99/32030. This prior art treatment essentially consists in distinguishing between the signals caused by the heart beat and the signals resulting from other variations in the flow of blood.

The signals from the units 18 and 19 are then analyzed in a unit 20 to eliminate artifacts due to movements of the wearer of the equipment by using the signals delivered by the accelerometric device 8 and preprocessed by the filtering and shaping means 18. This analysis is described in detail in the European patent application previously cited, with particular reference to FIG. 4 of that document, which may be consulted for more details.

The signal from the analysis unit 20 is fed to a block 20' which estimates the heart rate by determining the frequency of the intensity peaks of the signal from the unit 20, for example. The output signal of the unit 20', appearing at a terminal 21, is therefore representative of the heart beat or heart rate, and has been cleared of all artifacts that could influence the result of the measurement. As previously indicated, the sound reproduction unit B is connected to the transducer 3 through the cable C. The latter includes conductors for supplying power to the unit A from the power supply (not shown) conventionally provided in the sound reproduction unit B.

Note that the unit B can be adapted to reproduce in stereo sound information from a recording medium that the user has placed in it. Consequently, a second sound transducer can be provided in a second ear cushion for the wearer's other ear, as is conventional in off the shelf walkmans. For simplification, these components are neither shown nor described here.

In FIG. 2, the block 22 symbolizes means for reading a recording medium and producing a signal representative of a sound reproduction of what is recorded on the recording medium; these means being conventional, they are not described in detail.

According to the invention, the signal appearing at the terminal 21 and representative of the detected heart beat can be superimposed on the sound signals of the recording to which the user wishes to listen. To this end, the functional unit 1 already shown in FIG. 1 also provides various functions in addition to those already described, implemented in the blocks on the right-hand side in FIG. 2. These functions are described by way of example to illustrate the preferred embodiment of the invention. However, the invention is not limited to this description and can use simplified or more complex ways of implementing complementary functions.

This being so, in the version shown, the terminal 21 is connected to a voice synthesizer 23 which is in turn connected to a first mixer circuit 24 on the communication path between the unit 22 and the transducer 3. Thus the heart rate signal can be superimposed on the sound signals produced by the sound reproduction unit 22, for example with a given period that may be made adjustable.

The terminal 21 is also connected to a first input of a comparator 25 whose output is connected to a second mixer circuit 26 that is also on the path of the sound signals fed to the transducer 3. A second input of the comparator 25 is connected to a threshold generator 27 adapted to determine an alarm threshold corresponding to a heart rate value that is judged to be hazardous for the wearer of the equipment. The threshold generator 27 preferably allows adjustment of the alarm threshold. Consequently, if the measured heart rate exceeds the alarm threshold, an alarm signal can be superimposed on the sound signals sent to the transducer 3.

The voice synthesis and alarm threshold comparison functions just described can preferably be selected at will by the wearer of the equipment. To this end, a selector 28 is provided that can be accessed by means of a key (not shown) on the casing of the unit B, for example.

The terminal 21 can also be connected to a functional unit 29 for recording changes in the heart rate to retain a record thereof, advantageously on the recording medium that is being read in the unit 22 of the unit B. The functional unit 29 can be connected to an output terminal 30 of the unit B through which the latter can be connected to an external information processing device (not shown) for producing a medical analysis of the heart rate recording, for example.

Finally, a display screen 31 is advantageously provided (see FIG. 1) for visualizing the signal appearing at the terminal 21.

Figure 3:
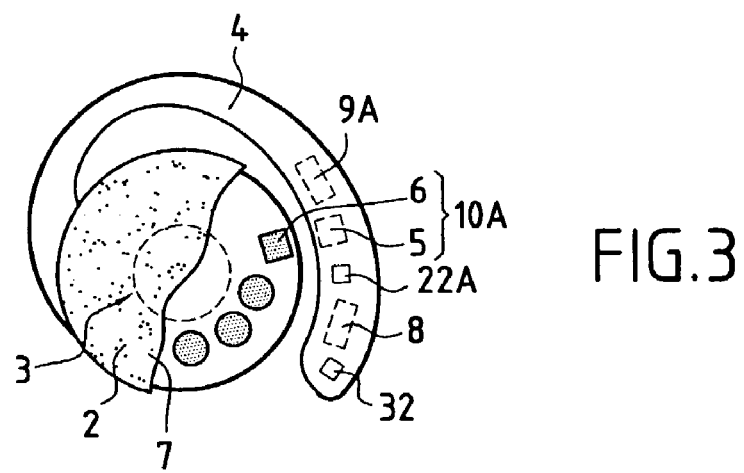
FIG. 3 is a diagrammatic representation of another embodiment of the invention.

FIG. 3 shows another embodiment of the invention in which the equipment constitutes a hearing aid. In this case, a sound reproduction unit 22A is provided including a microphone 32 for picking up ambient sounds. The sound reproduction unit 22A amplifies the signal from the microphone and sends the resulting signal to the transducer 3, which boosts it to a level sufficient for a hard of hearing wearer to perceive it. The transmission occurs via a mixer circuit (not shown in FIG. 3) analogous to the mixer circuits 24 and 26 shown in FIG. 2.

As in the embodiment shown in FIGS. 1 and 2, the measuring probe 10A includes a sender 5 and a receiver 6 which can be of the kind described already with reference to FIG. 2. It cooperates with a processing unit 9A which can be analogous to the processing unit 9 described above.

As shown in FIG. 3, the hearing aid is arranged as an ear cushion whose structure is the same as that of the ear cushion already described. However, in this case, all of the components of the equipment, and in particular the processing unit 9A and most of the other components, such as the units 23 and 24 from FIG. 2, are in the casing 2 and the horn 4, and powered by a battery (not shown), as is conventional in the hearing aid art.

The invention claimed is:

1. Portable equipment including in combination a measuring device for measuring the heart rate and a sound reproduction unit including means for supplying a signal representative of the sound reproduction and for supplying sound information to a sound transducer, wherein said measuring device and said sound transducer are mounted at least in part in an assembly adapted to be fixed to an ear of a wearer of the equipment, said sound reproduction unit includes substitution/superimposition means for optionally substituting for and/or superimposing on said signal representative of said sound reproduction a signal generated from signals from said measuring device and representative of said heart rate, said assembly takes the form of an ear cushion including a casing accommodating said sound transducer and adapted to be placed in front of the external auditory meatus opening of a wearer and a horn attached to said casing and adapted to be placed behind the external ear of a wearer and said measuring device is accommodated at least in part in said casing and at least in part in said horn, and said assembly further includes an accelerometric device delivering motion signals representative of the motion of a wearer when the assembly is fixed to an ear of said wearer and said measuring device including signal processing means using said motion signals for removing at least partially artifacts due to motion in said signal representative of said heart rate.

2. The portable equipment claimed in claim 1 wherein said measuring device includes an optical radiation emitter and an optical radiation receiver respectively placed in said casing and in said horn so that a light path between them can pass through a portion of the external ear of a wearer.

3. The portable equipment claimed in claim 2 wherein said optical radiation emitter includes a plurality of light sources emitting at separate wavelengths that are preferably near infra-red wavelengths.

4. The portable equipment claimed in claim 3 wherein said receiver includes the same number of groups of optical radiation detectors as there are light sources in said emitter and said measuring device further includes means for calculating the average of signals supplied by the detectors of each group.

5. The portable equipment claimed in claim 1 wherein said substitution/superimposition means of said sound reproduction unit include a mixer circuit adapted to receive said signal representative of said heart rate supplied by said measuring device and connected between said sound transducer and said means supplying said signal representative of the sound reproduction.

6. The portable equipment claimed in claim 5 wherein said sound reproduction unit includes voice synthesizer means connected between said probe and said mixer circuit.

7. The portable equipment claimed in claim 6 further including a comparator having a first input adapted to receive said signal representative of said heart rate and a second input connected to a threshold generator whose threshold is representative of a predetermined heart rate value and whose output is connected to said mixer circuit to send alarm information to said sound transducer if the heart rate supplied by said measuring device exceeds said predetermined heart rate value and wherein a selector is adapted to select reproduction by said sound transducer either of said alarm information or of said signal representative of said heart rate supplied by said measuring device.

8. The portable equipment claimed in claim 5 further including a comparator having a first input adapted to receive said signal representative of said heart rate and a second input connected to a threshold generator whose threshold is representative of a predetermined heart rate value and whose output is connected to said mixer circuit to send alarm information to said sound transducer if the heart rate supplied by said measuring device exceeds said predetermined heart rate value.

9. The portable equipment according to claim 1 wherein said sound reproduction unit includes a reader of a sound information medium, such as an audio cassette, a compact disc or a digital versatile disc, connected to said assembly by a cable.

10. The portable equipment according to claim 1 wherein said sound reproduction unit includes a microphone and constitutes a hearing aid.

* * * * *